United States Patent [19]

Kulik et al.

[11] Patent Number: 4,655,218

[45] Date of Patent: Apr. 7, 1987

[54] PROSTHETIC VALVE HOLDER

[75] Inventors: Yaroslav P. Kulik, Blagoveschensk; Ivan I. Shmyrin, Vladivostok; Rustam I. Utyamyshev, Moscow; Marina N. Vyrzhikovskaya; Boris A. Smirnov, both of Moscow, all of U.S.S.R.

[73] Assignee: Blagoveschensky Gosudarstuvenny Meditsinsky Institut, Blagoveschensk, U.S.S.R.

[21] Appl. No.: 786,246

[22] Filed: Oct. 10, 1985

[51] Int. Cl.[4] .................... A61B 17/28; A61M 29/00
[52] U.S. Cl. .................................. 128/321; 128/345; 623/2
[58] Field of Search ................ 128/321, 345, 303 R; 623/2

[56] References Cited

U.S. PATENT DOCUMENTS

| 1,328,624 | 1/1920 | Graham | 128/345 |
| 2,113,246 | 4/1938 | Wappler | 128/321 |
| 2,114,695 | 4/1938 | Anderson | 128/321 |
| 3,667,474 | 6/1972 | Lapkin et al. | 128/345 |
| 4,572,185 | 2/1986 | Rich | 128/321 X |

FOREIGN PATENT DOCUMENTS

| 0066465 | 12/1982 | European Pat. Off. | 128/321 |
| 881030 | 5/1953 | Fed. Rep. of Germany | 81/349 |
| 3335986 | 4/1985 | Fed. Rep. of Germany | 128/303 R |

Primary Examiner—William R. Cline
Assistant Examiner—Randolph A. Smith
Attorney, Agent, or Firm—Fleit, Jacobson, Cohn & Price

[57] ABSTRACT

A holder of a valve prosthesis implantable in a patient's circulatory system, including arms which have handles at one of their ends, and three or more working jaws provided at the end thereof for a valve prosthesis to secure thereon. The ends of all the working jaws form a circle when brought apart.

3 Claims, 4 Drawing Figures

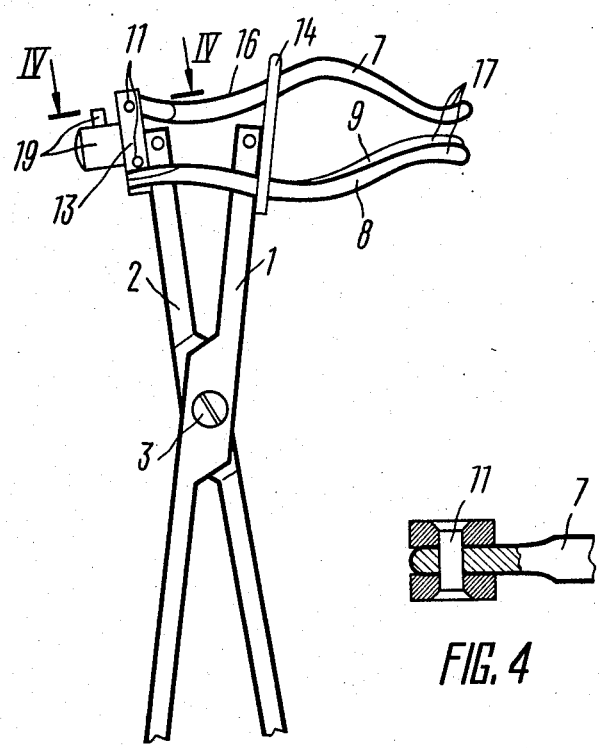
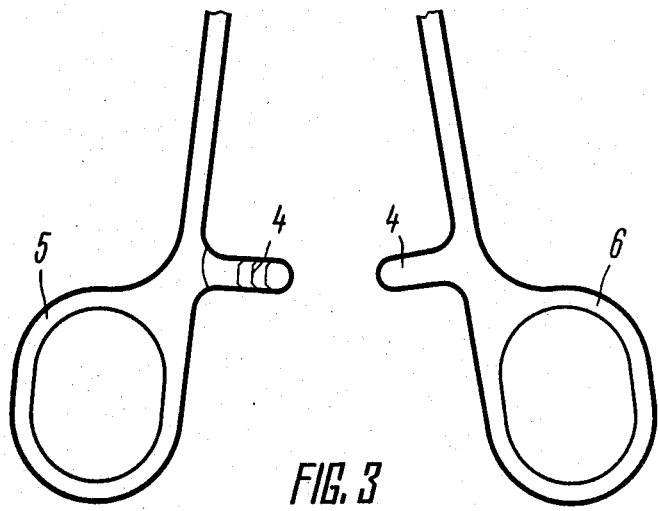
FIG. 4
FIG. 3

PROSTHETIC VALVE HOLDER

FIELD OF THE INVENTION

This invention relates generally to surgical instruments and more specifically to a prosthetic valve holder.

The invention can find application for implanting valve prostheses in a patient's circulatory system, i.e. thoracic surgery during operative intervention on the heart, e.g., in application of cardiac valve prostheses.

BACKGROUND ART

Known in the present state of the art are holders for cardiac valve prosthesis, shaped as a straight rod with a screw-and-nut actuator and gripping jaws. (cf., e.g. the Catalogue of MERA, p. 11, items LB 1085, LB 1086).

A disadvantage inherent in the known holders mentioned above resides in that, when manipulating such holders a surgeon's assistant with his hands obstructs partially or overlaps the operative field, and the screw-and-nut actuator takes much time for a valve prosthesis to hold and remove.

One more prior-art holder is known to comprise two arms joined together through a pivot pin and having at one of their ends handles with a box lock, and at the other end, two working jaws for a valve prosthesis to secure thereon (cf., e.g., the Catalogue of MERA, p. 11, item LB 1005).

However, said known holder fails to hold the valve prosthesis reliably in the course of surgery, since the valve is fixed in place with two arms, i.e., actually at two points only, and also fails to provide rigid holding of the valve in the holder, which offers some difficulties and inconveniences in stitching the valve prosthesis in position.

In addition, when involved in fitting a valve prosthesis on the atrioventricular fibrous ring, the known holder fails to provide quick and complete contact between the prosthesis and said ring and require further manipulations for the purpose.

SUMMARY OF THE INVENTION

It is an object of the present invention to provide a prosthetic valve holder which would be instrumental during surgery in quick and exact apposition of the prosthetic valve surface with that of the atrioventricular fibrous ring.

It is another object of the present invention to provide such a prosthetic valve holder that would fix the valve reliably in position.

It is still another object of the present invention to provide favourable conditions for the valve to be quickly fixed on or removed from the holder.

It is a still further object of the present invention to rule out any possibility of overlapping or even complete obstruction of the operative field during the valve fitting procedure.

It is an additional object of the present invention to cut down the operating time.

The aforesaid objects are accomplished due to the fact that the holder of a valve prosthesis implantable in a patient's circulatory system, according to the invention, comprises two hinge-joined arms, handles provided at one end of each arm, and at least three working jaws secured at the other end of either of said arms and so arranged that their vacant ends, when brought apart, form a circle along their perimeter.

It is expedient that all the working jaws be arranged at an angle of 90° to the holder longitudinal axis and be fitted at the arm end articulately.

At the other arm's end there may be secured a plate with a number of slots, each of these corresponding to its own working jaw so that the working jaws are passed through said slots with a possibility of free traversing through said slots when being brought apart or together.

It is also expedient that each of the working jaws be curved and that for said jaws to be brought apart or together, the edge of each of said slots should slide along the curved portion of the respective working jaw.

It is likewise expedient that a projection be provided on the arm that carries the working jaws, on the arm side opposite to said jaws, for a ligature-holder to secure, and that a lock be provided on said projection.

The proposed prosthetic valve holder is capable of providing reliable attachment of a valve prosthesis therein, quick and exact apposition of the surface of said valve prosthesis with that of the atrioventricular fibrous ring, cutting down the operating time due to rapid fixing the valve on and removing it from the holder, and ruling out any possibility of overlapping or complete obstruction of the operative field.

DETAILED DESCRIPTION OF THE INVENTION

Other objects and advantages of the present invention will become apparent from a consideration of some specific exemplary embodiments thereof described hereinbelow with reference to the accompanying drawings, wherein:

FIG. 3 is a prosthetic valve holder, according to the invention, with the working jaws brought together; and FIG. 4 is a view of same holder, taken along the line IV—IV in FIG. 3.

Figures 1, 2:
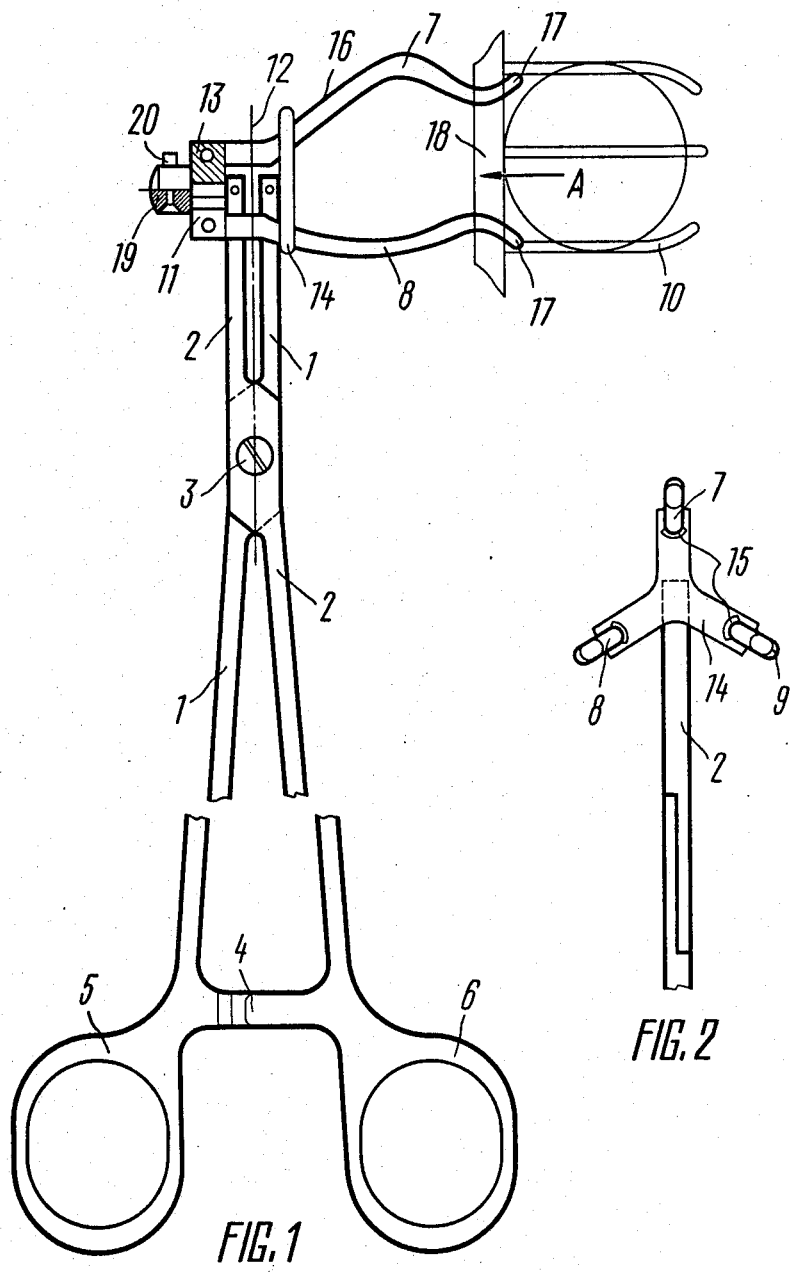
FIG. 1 is a fragmentary sectional view of a prosthetic valve holder, according to the invention.
FIG. 2 is a view of same holder, taken along the arrow A in FIG. 1.

The holder of a valve prosthesis, e.g., a cardiac valve prosthesis, comprises two arms 1, 2 (FIG. 1) interconnected through a hinge 3 and having a box lock 4. One of the ends of each arm 1, 2 is provided with a handle 5 or 6, respectively. The other end of the arm 2 carries three working jaws 7, 8, 9 (FIG. 2). The ends of the working jaws 7 to 9 form, when brought apart, a circle and are equispaced therealong, i.e., the working jaws 7 to 9 are spaced 120 degrees apart in the plane of the circumference passing through their working ends.

The working jaws 7 to 9 may be increased in number, while their ends should be equispaced apart peripherally as described above. Provision of the three or more working jaws 7 to 9 affords reliable fixing of a valve prosthesis 10 (FIG. 1) thereon, since the valve rests on at least three points of support.

The working jaws 7 to 9 are articulated to the arm 2 through pivots 11 and make up an angle of 90° with a longitudinal geometric axis 12 of the holder, which rules out overlapping of the operative field during the fitting procedure of the valve 10. The pivots 11 are mounted on a plate 13 provided on the arm 2.

It should be recognized that the most convenient and technologically acceptable embodiment of the holder is the one, wherein the arm 1 carries a plate 14 provided with slots 15 equal in number with that of the working jaws 7 to 9. Each of the working jaws 7, 8, 9 is passed through the respective slot 15 which is made in such a manner that the working jaw 7 (or 8, 9) would be free to travel along the slot 15 when the jaws 7 to 9 are brought apart or together. The plate 14 may be a shaped one as shown in FIG. 2.

Besides, the plate 14 (FIG. 1) provided with slots 15 may perform the functions of an actuator for the working jaws 7 to 9 to bring them together or apart. Such being the case, the jaws 7 to 9 are bent at an angle to the plate 14, whereby the edge of each slot 15 is free to slide along a curved portion 16 of the jaw 7 (8 or 9).

Opposite ends 17 of the jaws 7 to 9 are also bent to suit the diameter of a collar 18 of the valve prosthesis 10 in order to hold the latter more tightly.

The holder construction discussed herein enables it to be provided with a means for attaching a ligature-holder, which is of great convenience to carry out and expedite surgery. To this end, a projection 19 is provided on the arm 2 carrying the working jaws 7 to 9, arranged oppositely to the latter, a lock 20 in the form of a pin being located on said projection 19.

The prosthetic valve holder of the invention functions as follows.

To site the valve prosthesis 10 onto the working jaws 7 to 9, the shorter ends of the arms 1, 2 are brought together with the aid of their handles 5, 6. As a result, each of the jaws 7 to 9 turns about its own pivot 11 and slides along the edge of the respective slot 15 with its curved end 16, while the opposite ends 17 of the jaws are brought towards the centre of a circle thus formed by said ends.

Then the ends 17 of the working jaws 7 to 9 are introduced into the collar 18 of the valve prosthesis 10, and the jaws are brought as far apart as to suit the size of the valve prosthesis 10. As a result, the collar 18 of the valve 10 is held reliably at the ends 17, which are so curved as to suit the cross-sectional diameter of the collar 18.

With this purpose in view, those ends of the arms 1, 2 are to be brought together on which the handles 5, 6 are provided. In this case the opposite ends of the arms 1, 2 are also brought together, while the working jaws 7 to 9, while each turning around its own pivot 11 and sliding with its curved portion 16 along the edge of the respective slot 15 in the plate 14, get brought apart and their ends 17 are set in the plane of the circumference of the collar 18 of the valve 10.

The prosthetic valve holder of the invention enables a valve prosthesis to be fit in place rapidly and accurately, since it is capable of exactly apposing the surface of the valve prosthesis collar with that of the atrioventricular fibrous ring. This is attainable due to reliable fixing of the valve in the holder, a possibility of quickly fixing the valve on and removing it from the holder, ruling out any possibility of overlapping or complete obstruction of the operative field, thus affording good observability of the operative field and convenient stitching of the valve prosthesis to the atrioventricular fibrous ring. All this cuts down to a great extent the operating time, renders the surgery for correction of valvular defects more accurate, and yields good results within the postoperative period.

What is claimed is:

1. A holder of a valve prosthesis implantable in a patient's circulatory system, comprising:

a first arm and a second arm hinge-joined to each other; said first arm having a first end and a second end; said second arm having a first end and a second end;

handles provided at said first ends of said first and second arms;

at least three similar working jaws, which can be brought together for a valve prosthesis to set thereon, and be brought apart for said valve prosthesis to hold thereto, thus giving said valve at least three bearing points;

said working jaws pivotally mounted at said second end of said first arm and having vacant ends which, when brought apart, define a circle along their perimeter;

a plate having a plurality of slots equal in number to that of said working jaws; said plate being secured at said second end of said second arm in such a manner that one of said working jaws is passed through each of said slots so that when said working jaws are being brought together or apart, they are free to traverse along said slots.

2. A holder as claimed in claim 1, wherein said working jaws are curved, and for said jaws to be brought together and apart, the edge of each of said slots slides along said curved working jaw passing through said slot.

3. A holder of a valve prosthesis implantable in a patient's curculatory system, comprising:

a first arm and a second arm hinge-joined to each other;

said first arm having a first end and a second end;

said second arm having a first end and a second end;

handles provided at said first ends of said first and second arms;

at least three similar working jaws, which can be brought together for a valve prosthesis to set thereon, and be brought apart for said valve prosthesis to hold thereto, thus giving said valve at least three points of bearing; said working jaws being articulated to said second end of said first arm and having vacant ends which, when brought apart, form a circle along their perimeter; said at least three working jaws, each of them being arranged at an angle of 90° to a longitudinal geometric axis of the holder;

said working jaws being of a curved shape;

a plate having a plurality of slots equal in number to that of said working jaws; said plate being secured at said second end of said second arm in such a manner that one of said working jaws is passed through each of said slots so that when said working jaws are being brought together or apart, they are free to traverse along said slots, and the edge of each of said slots slides along said curved working jaw passing through said slot.

* * * * *